US005580983A

United States Patent [19]

Kraus

[11] Patent Number: 5,580,983
[45] Date of Patent: Dec. 3, 1996

[54] PROCESS FOR THE PREPARATION OF N-ACYLATED 2-CHLORO-5-AMINOMETHYLPYRIDINES

[75] Inventor: Helmut Kraus, Odenthal, Germany

[73] Assignee: Bayer Aktiengesellschaft, Leverkusen, Germany

[21] Appl. No.: 495,008

[22] Filed: Jun. 27, 1995

[30] Foreign Application Priority Data

Jul. 4, 1994 [DE] Germany ............................ 44 23 353.1

[51] Int. Cl.⁶ .................................................. C07D 213/56
[52] U.S. Cl. ........................ 546/336; 546/262; 546/337; 546/194; 546/269.7; 546/271.1; 546/271.4; 546/272.1; 546/276.4; 546/274.7; 546/275.4; 546/279.1; 546/280.4; 546/284.7
[58] Field of Search ...................................... 546/336, 337

[56] References Cited

U.S. PATENT DOCUMENTS

| 5,300,650 | 4/1994 | Nabata | 546/329 |
| 5,382,671 | 1/1995 | Diehr | 546/329 |
| 5,453,506 | 9/1995 | Diehr | 546/329 |

FOREIGN PATENT DOCUMENTS

| 0303389 | 2/1989 | European Pat. Off. . |
| 0302389 | 2/1989 | European Pat. Off. . |
| 0366085 | 5/1990 | European Pat. Off. . |
| 0376279 | 7/1990 | European Pat. Off. . |
| 0556684 | 8/1993 | European Pat. Off. . |
| 0579970 | 1/1994 | European Pat. Off. . |
| 3726993 | 2/1989 | Germany . |
| 4222152 | 1/1994 | Germany . |
| 9310099 | 5/1993 | WIPO . |

OTHER PUBLICATIONS

English translation of DE 42 22 152, (Jan. 13, 1994).
E. Müller, Mehtoden der Organischen Chemie (Houben-–Weyl), 4, vol. XI/1, pp. 556–557, Georg Thieme Verlag, Stuttgart, (1957).
Patent Abstracts of Japan, vol. 18, No. 75, abstract of JP–05–286936, (1994).

*Primary Examiner*—Amelia Owens
*Attorney, Agent, or Firm*—Sprung Horn Kramer & Woods

[57] ABSTRACT

2-Chloro-5-(N-acyl-aminomethyl)pyridines can be prepared by hydrogenation of 2-chloro-5-cyanopyridine with hydrogen in an acylating agent using a hydrogenation catalyst.

5 Claims, No Drawings

PROCESS FOR THE PREPARATION OF N-ACYLATED 2-CHLORO-5-AMINOMETHYLPYRIDINES

The invention relates to a process for the preparation of 2-chloro-5-(N-acyl-aminomethyl)-pyridines by hydrogenation of 2-chloro-5-cyanopyridine in the presence of an acylating agent.

2-Chloro-5-(N-acyl-aminomethyl)-pyridines are important components for the preparation of insecticides of the nitromethylene class: on the one hand 2-chloro-5-aminomethylpyridine can be obtained by splitting off the acyl group, and on the other hand 2-chloro-5-N-alkyl-aminomethylpyridine can be obtained by hydrogenation or by alkylation and subsequent splitting off of the acyl group. The N-methyl, N-ethyl and N-aminoethyl compounds are particularly important (EP-A 303 389, 366 085 and 376 279).

Hydrogenations of 2-chloro-5-cyanopyridine have been described in several instances. To avoid the formation of secondary amines, the reaction is usually carded out in the presence of ammonia or tertiary amines (DE-A 3 726 993 and 4 222 152 and U.S. Pat. No. 5,300,650). Recommended solvents are (optionally aqueous) alcohols or aromatics or non-polar aprotic solvents. It has also already been proposed to react 2-chloro-5-aminomethylpyridine with formic acid, to alkylate the 2-chloro-5-formylaminomethyl-pyridine formed without intermediate isolation and to split off the formyl group again from the resulting 2-chloro-5-N-alkyl-N-formyl-aminomethyl)pyridine (EP-A 556 684). These processes are either cumbersome, or are unsatisfactory in view of the yield; if they require the me of ammonia, the associated measures make it more expensive to carry them out on an industrial scale.

Surprisingly it has been found that the preparation of the desired products is effected in an ammonia-flee process With a very high yield if the hydrogenation is carried out in the presence of the acylating agent.

The invention thus relates to a process for the preparation of compounds of the formula

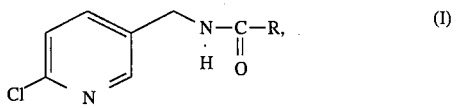

wherein

R denotes hydrogen, $C_1$–$C_8$-alkyl, $C_1$–$C_8$-halogenoalkyl, $C_2$–$C_8$-alkenyl, alkoxyalkyl having 2 to 8 C atoms, alkoxyalkenyl having 3 to 8 C atoms, $C_3$–$C_8$-cycloalkyl, $C_6$–$C_{12}$-aryl, $C_7$–$C_{10}$-aralkyl, a protected hydroxy-$C_4$–$C_6$-alkyl group, a protected amino-$C_4$–$C_6$-alkyl group or a 5- to 8-membered ring having 1 or 2 heteroatoms from the series consisting of N, O and S, by catalytic hydrogenation of 2-chloro-5-cyanopyridine with hydrogen in the presence of an acylating agent.

"$C_1$–$C_8$-Alkyl" includes linear and branched radicals, such as, for example, methyl, ethyl, propyl, isopropyl, butyl, isobutyl, tert-butyl and the isomeric amyls, hexyls and octyls, preferably the $C_1$–$C_4$-alkyl radicals mentioned.

"$C_1$–$C_8$-Halogenoalkyl" includes linear and branched radicals, such as, for example, chloromethyl, 1-chloroethyl, trifluommethyl, 2-bromoethyl, 2-chloroisopropyl and 5-fluorooctyl, but preferably chloro-, fluoro- or bromoalkyl radicals having 1 to 4 C atoms.

"$C_2$–$C_8$-Alkenyl" includes, for example, vinyl, allyl, the isomeric butenyls, amylenyls, hexenyls or octenyls, preferably the $C_3$–$C_4$-alkenyl radicals mentioned.

"Alkoxyalkyl having 2 to 8 C atoms" includes, for example, methoxymethyl, methoxyethyl and further radicals from the group consisting of $C_3$–$C_9$-alkyl in which one $CH_2$ group is replaced by an O atom.

"Alkoxyalkenyl having 3 to 8 C atoms" includes, for example, methoxyallyl, 2-methoxy-propenyl and other radicals from the group consisting of $C_4$–$C_9$-alkenyl wherein a $CH_2$ group is replaced by an O atom.

"$C_3$–$C_8$-Cycloalkyl" includes, for example, cyclopropyl, methylcyclopropyl, dimethylcyclopropyl, methylcyclobutyl, cyclopentyl, methyl-cyclopentyl, cyclohexyl, methylcyclohexyl, dimethyl-cyclohexyl, cycloheptyl and cyclooctyl, preferably cyclopropyl, cyclopentyl and cyclohexyl, and methyl or dimethyl substitution products thereof.

"$C_6$–$C_{12}$-Aryl" includes, for example, phenyl, naphthyl and phenyl which is optionally substituted 1 to 3 times by identical or different substituents, substituents which may be mentioned being:

fluorine, chlorine, bromine, iodine, cyano, nitro, hydroxy, amino, mercapto, methyl, ethyl, n-propyl or i-propyl, n-butyl, s-butyl, i-butyl or t-butyl, trifluoromethyl, trichloromethyl, difluoromethyl, methoxy, ethoxy, methylthio, ethylthio, trifluoromethoxy, difluoromethoxy, trifluordmethylthio, chlorodifluoromethylthio, vinyl, 2-propenyl, 2-propinyl, 2-propinyloxy, 2-propinyloxy, cyclopropyl, cyclopentyl, cyclohexyl, phenyl, phenoxy, phenylthio, phenylmethoxy, phenylmethylthio, methylamino, dimethylamino, ethylamino, diethylamino, pyrrolidino, piperidino, morpholino, thiomorpholino, N-methylpiperazino, 2,6-dimethylmorpholino, phenylamino, hydrazino, 2-methylhydrazo, 2,2-dimethylhydrazo, 2-phenylhydrazo, methylcarbonylamino, phenylcarbonylamino, aminocarbonyl, methylaminocarbonyl, dimethylaminocarbonyl, methoxycarbonyl or ethoxycarbonyl.

"$C_7$–$C_{10}$-Aralkyl" includes, for example, 1- and 2-phenethyl, preferably benzyl.

Protective groups for hydroxy-$C_4$–$C_6$-alkyl groups and for amino-$C_4$–$C_6$-alkyl groups are $C_1$–$C_{18}$-acyl groups, in particular acetyl groups.

Examples of 5- to 8-membered heterocyclic rings include pyrrole, furan, thiophene, pyrrolidine, pyrazole, imidazole, thiazole, oxazole, pyridine, pyrimidine, piperazine, morpholine, pyran, azepine, azocine, isoxazole, isothiazole, pyridazine and pyrazine.

The acylating agents suitable for the process according to the invention include acids of the formula RCOOH, wherein R has the meaning given in formula (I), and the anhydrides, acid chlorides and $C_1$–$C_4$-alkyl esters of these acids, such as, for example, methyl formate, ethyl formate, trifluoroacetic acid, 3-chloropropionyl chloride, acetic anhydride, acetyl formate, trifluoroacetic anhydride and benzoyl chloride.

The weight ratio of the starting substance (2-chloro-5-cyanopyridine) to the acylating agent can vary within wide limits; in general, it is 1:1 to 1:100, preferably 1:2 to 1:50. An inert organic solvent can be added to the acylating agent for dilution. Examples of such organic solvents include hydrocarbons having 6 to 15 C atoms, such as n-hexane, n-heptane, cyclohexane, benzene and toluene. Preferably, the weight of the inorganic solvent does not exceed the weight of the acylating agent; according to a preferred embodiment, the organic solvent is dispensed with and the hydrogenation is carded out in excess acylating agent instead.

The hydrogenation takes place in the presence of hydrogenation catalysts, such as are described, for example, in "Methoden der Organischen Chemie" [Methods of Organic Chemistry](Houben-Weyl), 4th edition, Volume XI/1, Georg Thieme Verlag, Stuttgart, 1957. Raney catalysts, in particular Raney nickel and Raney cobalt, are preferred. The catalysts are preferably employed in amounts of 3 to 50, in particular 5 to 35% by weight based on the 2-chloro-5-cyanopyridine.

Hydrogen is used as the hydrogenating agent. The hydrogenation is usually carried out under a pressure of 5 to 300, preferably 50 to 200 bar.

The hydrogenation can be carried out within a wide temperature range. As a role, it is carried out at a temperature of 20 to 150, preferably 50 to 130 and specifically 70° to 110° C.

In a preferred embodiment; the chlorocyanopyridine, acylating agent, diluted with solvent if appropriate, and the catalyst are initially introduced into an autoclave. Hydrogen is then metered in, while heating up the mixture, until the desired pressure and temperature are reached, and hydrogenation is carried out until the end of the uptake of hydrogen, while maintaining these parameters.

The percentage data of the following examples in each case relate to the weight.

EXAMPLES

Example 1

15.0 g of 91.7% pure (0.1 mol) 2-chloro-5-cyanopyridine (crude goods from the reaction of dimethylaminoglutaconic acid dinitrile with hydrogen chloride in 1,2-dichloroethhane/dimethylformamide) were hydrogenated in 50 g of toluene and 50 g of acetic anhydride using 3.5 g of Raney cobalt in a 0.3 l V4A autoclave for 8 hours under a hydrogen pressure of 200 bar and at 100° C. After the catalyst had been filtered off, the low-boiling constituents were distilled off. The residue (21.3 g) comprised 2-chloro-5-(acetylaminomethyl)-pyridine to the extent of 65.7%, corresponding to 76.2% of theory. The product could be purified by recrystallization from ethanol.

Example 2

15 g of 91.7% pure (0.1 mol) 2-chloro-5-cyanopyridine were hydrogenated in a mixture of 70 ml of methylformate and 50 ml of toluene analogously to Example 1. After analysis by gas chromatography, 2-chloro-5-(formylaminomethyl)pyridine had formed in a yield of 86.7% of theory. 2-Chloro-5-(aminomethyl)pyridine (3.6% of theory) and di(2-chloro-5-methylpyridyl)amine (2.0% of theory) were identified as by-products. The crude product was boiled under reflux with 30 ml of 20% strength NaOH for 2 hours. After extraction with $CH_2Cl_2$ and concentration, the residue was distilled in vacuo. 12 g of 98.7% pure goods, corresponding to 83.1% of theory, based on the 2-chloro-5-cyanopyridine, were obtained.

Example 3

99.3% pure 2-chloro-5-cyanopyridine was reacted analogously to Example 2. 2-Chloro-5-(formylaminomethyl)pyridine were obtained as 85% pure goods in a yield of 85.9% of theory.

Example 4

30 g of 91.7% pure 2-chloro-5-cyanopyridine were hydrogenated in 100 ml of methylformate using 7 g of Raney cobalt analogously to Example 2. 2-Chloro-5-(formylaminomethyl)pyridine was obtained in a yield of 92.6% of theory, in addition to 2.9% of theory of 2-chloro-5-(aminomethyl)pyridine.

Example 5

99.3% pure goods were hydrogenated analogously to Example 4. The yield was 91.8% of theory.

I claim:

1. Process for the preparation of compounds of the formula

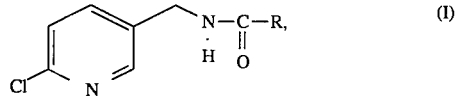

wherein

R denotes hydrogen, $C_1$–$C_8$-alkyl, $C_1$–$C_8$-halogenoalkyl, $C_2$–$C_8$-alkenyl, alkoxyalkyl having 2 to 8 C atoms, alkoxyalkenyl having 3 to 8 C atoms, $C_3$–$C_8$-cycloalkyl, $C_6$–$C_{12}$-aryl, $C_7$–$C_{10}$-aralkyl, a protected hydroxy-$C_4$-$C_6$-alkyl group, a protected amino-$C_4$–$C_6$-alkyl group or a 5- to 8-membered ting having 1 or 2 heteroatoms from the series consisting of N, O and S, by catalytic hydrogenation of 2-chloro-5-cyanopyridine with hydrogen in the presence of an acylating agent.

2. Process according to claim 1, in which the reaction medium is diluted with an inert organic solvent, the weight of which does not exceed the weight of the acylating agent.

3. Process according to claim 1, in which the hydrogenation is carried out under a pressure of 5 to 300 bar.

4. Process according to claim 1, in which the hydrogenation is carded out at a temperature of 20° to 150° C.

5. Process according to claim 1, in which Raney nickel or Raney cobalt is used as the hydrogenation catalyst.

* * * * *

UNITED STATES PATENT AND TRADEMARK OFFICE
CERTIFICATE OF CORRECTION

PATENT NO. : 5,580,983
DATED : December 3, 1996
INVENTOR(S) : Kraus, Helmut

It is certified that error appears in the above-indentified patent and that said Letters Patent is hereby corrected as shown below:

Col. 4, line 35    Delete " ting " and substitute
                   -- ring --

Signed and Sealed this

Twenty-second Day of April, 1997

*Attest:*

BRUCE LEHMAN

*Commissioner of Patents and Trademarks*

*Attesting Officer*